US006939535B2

(12) United States Patent
Cozean et al.

(10) Patent No.: US 6,939,535 B2
(45) Date of Patent: Sep. 6, 2005

(54) METHOD AND APPARATUS FOR PREVENTING TOOTH DECAY

(75) Inventors: Colette Cozean, Lake Forest, CA (US); Lynn Powell, Salt Lake City, UT (US); Samir Nammour, Brussels (BE)

(73) Assignee: Nocari, LLC, Lake Forest, CA (US)

(*) Notice: Subject to any disclaimer, the term of this patent is extended or adjusted under 35 U.S.C. 154(b) by 0 days.

(21) Appl. No.: 10/039,291

(22) Filed: Jan. 3, 2002

(65) Prior Publication Data

US 2002/0164291 A1 Nov. 7, 2002

Related U.S. Application Data

(60) Provisional application No. 60/259,668, filed on Jan. 3, 2001.

(51) Int. Cl.$^7$ ............................. A61K 7/16; A61K 7/18; A61K 7/20; A61C 5/00
(52) U.S. Cl. ........................... 424/52; 514/835; 433/29; 433/80; 433/82; 433/84; 433/89; 433/114; 433/125; 433/141; 433/142; 433/215
(58) Field of Search ......................... 424/52; 514/835; 433/29, 80, 82, 84, 89, 114, 125, 141, 142, 215

(56) References Cited

U.S. PATENT DOCUMENTS

| | | | |
|---|---|---|---|
| 4,273,535 A | | 6/1981 | Yamamoto et al. |
| 5,762,493 A | * | 6/1998 | Rechmann .................. 433/29 |
| 6,026,828 A | | 2/2000 | Altshuler |
| 6,102,696 A | | 8/2000 | Osterwalder et al. |
| 6,419,905 B1 | * | 7/2002 | Alvarez Hernandez ...... 424/53 |
| 6,439,888 B1 | * | 8/2002 | Boutoussov et al. ........ 433/215 |
| 6,764,309 B2 | * | 7/2004 | Cozean et al. .............. 433/215 |

FOREIGN PATENT DOCUMENTS

| | | |
|---|---|---|
| DE | 100 09 004 A | 10/2001 |
| EP | 0 743 029 A | 11/1996 |
| WO | WO 98 58595 A | 12/1998 |

OTHER PUBLICATIONS

"Argon laser effect on demineralization of human enamel" by G. Lynn Powell, Laser Surgery, 1992, vol. 1643, pp. 374–379.

"Combined effects of argon laser irradiation and fluoride treatments in prevention of caries–like lesion formation in enamel: an in vitro study" by Syed M. Haider et al., The Journal of Clinical Pediatric Dentistry, 1999, vol. 23, No. 3, pp. 247–256.

"Effects of Laser Irradiation on Occlusal Surfaces of Human Molars." By R.L. Slayton and J.S. Wepel, 1991 IADR Abstract, No. 1818.

"Treating Occlusal Pit and Fissure Surfaces by IR Laser Irradiation" by Douglas A. Young, Daniel Fried, and John D.B. Featherstone. SPIE vol. 3810 (2000).

"Nd: YAG Laser in Caries Prevention: a Clinical Study" by D.M. Zezell, H.G.D. Boari, C.P. Eduardo. Abstract and Presentation from 1$^{st}$ Congress—European Society for Oral Laser Applications, Vienna, Austria. May 17–20, 2001.

Proceedings of "Third International Congress on Lasers in Dentistry", pp. 41–42, Salt Lake City, Utah. Aug. 6–8, 1992.

* cited by examiner

*Primary Examiner*—Frederick Krass
(74) *Attorney, Agent, or Firm*—Knobbe, Martens, Olson & Bear, LLP

(57) ABSTRACT

A method for preventing tooth decay by initially treating the tooth surface with a laser with a coherent or noncoherent light source. This process makes the tooth more resistant to acid and more able to bond fluoride, thus requiring a lower concentration of fluoride. The method allows for a deeper penetration of the tooth then previously accomplished with other methods.

21 Claims, No Drawings

METHOD AND APPARATUS FOR PREVENTING TOOTH DECAY

PRIORITY APPLICATIONS

This application claims priority of U.S. Provisional application 60/259,668, filed Jan. 3, 2001, herein incorporated by reference.

FIELD OF THE INVENTION

This invention relates to a method and an apparatus for preventing tooth decay. More specifically, the invention relates to using a visible light beam or electromagnetic radiation treatment and subsequent low concentration fluoride treatment to prevent tooth decay.

BACKGROUND OF THE INVENTION

Tooth decay is caused by demineralization of the tooth structure at either the enamel or root surface. The enamel is a thin layer (1–2 mm) composed of a crystal-type structure of hydroxyapatite or Calcium phosphate hydroxide, containing large amounts of Calcium and Phosphorus. Dental enamel is a porous material and although it contains about 96% by weight of mineral, this is equivalent to approximately 85 percent by volume. The remaining 15 percent by volume is made up of water, protein and lipid, which form the diffusion channels though which acids and minerals can travel in or out of the tooth. The dentin, the major part of the core of the tooth, is composed of $CaCO_3$, a chalk-like material. Although it is 70% by weight of mineral, it also contains 20% by weight organic and 10% by weight water. This corresponds to 47% by volume mineral.

Tooth decay, or dental caries results from the growth of bacteria on the tooth. The bacteria metabolize sugars to acid and this dissolves the tooth. The bacteria grow as a plaque on the tooth and treatment involves periodic removal of the plaque and strengthening of the tooth to make it more resistant to the acid produced by the bacteria.

Other professional methods to prevent tooth decay have included fluoride, pit and fissure sealants, and varnishes. However, none of these methods individually protect all of the tooth surfaces nor are they permanent, usually lasting less than 5 years. In addition, heat treatment has been explored as an alternative method. By treating the tooth with a very high heat, from 250–1000° C., the structure of the tooth is changed, making it more resistant to acid. This method has never been used clinically because of safety concerns. Because most of the changes to the tooth occur at a very high heat, 1200° C., some changes occur between 500° C. and 1000° C. and a few were seen at temperatures as low as 250° C. to 400° C., there is the potential for thermal damage to the underlying pulpal tissue, adjacent soft tissue and osseous structures. Therefore, although the effects of laser irradiation on dental caries and tooth structure were explored some 30 years ago, the risk of thermal damage to the adjacent hard tissue and pulp was such that much of the research was abandoned. Several laser wavelengths have been explored, including $CO_2$ and Nd:YAG, but both produce a significant amount of heat on the surface of the tooth and in the pulp and provide only a shallow treatment of the tooth itself. With improved laser technology, a number of different types of lasers with varying tissue penetration and energy levels have been developed.

The structural changes produced by the application of heat by $CO_2$ and Nd:YAG lasers at these very high heats includes a change in the phosphate molecule in the hydroxyapatite. This makes the tooth less soluble and increases resistance to decay. However, the level of heat produced by these lasers has not been used clinically because it has been shown to damage the tooth structure itself as well as potentially damaging soft tissue.

The action of the laser, as well as other types of tooth treatments, to produce resistance of the tooth to acid can be envisioned as follows: it has been hypothesized that tooth enamel crystals ("hydroxyapatite") possess two types of sites from which dissolution can occur. The first type of site (the "thermal" site) is less resistant to dissolution by acids under conditions typically found in the oral environment than is the second type of site (the "chemical" site). The treatment of tooth enamel by carbon dioxide laser irradiation or by high temperatures eliminates or reduces the thermal sites, leaving only the chemical sites for dissolution to occur. Once the thermal sites have been eliminated, the tooth enamel is then treated to eliminate the chemical sites with dissolution rate inhibitors or chemical agents. However, even if such laser treatments were clinically usable for safety reasons, they have the disadvantage that they produce only a surface treatment and cannot protect all of the tooth structure.

Therefore, all of these methods are rendered undesirable by that fact that they can only provide temporary treatment, act only at a very shallow depth of the tooth, and some cannot be used due to safety issues. In addition, none of the above methods can be used in a non-professional setting.

SUMMARY OF THE INVENTION

The invention provides a composition for preventing tooth decay in a tooth treated with electromagnetic radiation having fluoride at a concentration of less than 45 ppm fluoride to (0.01%) to 0.002 ppm fluoride. The composition may be a mouthwash, a patch, or a toothpaste.

The invention provides a method of treating a tooth by irradiating the tooth with a light beam, having wavelengths in the range of between from about 400 nm to about 810 nm, and irradiating by exposing the tooth to an energy and an energy density sufficient to vaporize organic material without damaging the tooth structure.

A further embodiment involves bonding a chemical agent to the crystalline structures of the tooth after removal of the organic compound. Preferably the chemical agent is fluoride. Preferably the effective concentration of fluoride is less than or equal to 200 ppm of stannous fluoride (0.08%) or 1000 ppm of sodium fluoride (0.275%). Preferably, the fluoride acts by binding to hydroxide groups within the hydroxyapatite crystal. Preferably, the fluoride penetrates to the subsurface more than 0.1 microns.

The light beam may be a coherent or noncoherent light source. Preferably, it is a laser, more preferably an argon laser. Preferably, the wavelength of the laser is selected from the group consisting of: red, green, blue, and yellow lasers. Alternatively, a noncoherent light source may be an LED, preferably having a wavelength from the IR spectra selected from the group consisting of green, blue, yellow, and red light.

Preferably, the argon laser beam is applied at 250 mJ for 10 seconds for each treated surface. Preferably, the tooth is treated for a period of time of more than 1 sec for each treated surface. Preferably, the light beam has an energy density below about 65 $J/cm^2$, even more preferably, 30 $J/cm^2$ and even more preferably, 12 $J/cm^2$.

Preferably, the treatment heats the tooth structure to a temperature less than about 250° C. Alternatively, the treatment heats the tooth structure to a temperature less than about 100° C., alternatively, less than about 50° C. The tooth structure which is being heated may specifically be localized sites containing concentrations of water and/or organic materials.

In a further embodiment, the method includes treating with fluoridated mouthwash, toothpaste, or a patch after treatment. Preferably, the mouthwash contains 45 ppm fluoride to (0.01%) to 0.002 ppm fluoride. Preferably, the fluoride is applied for 1 day to 80 years.

A further embodiment is a method which reduces the a axis of a crystal of hydroxyapatite in a tooth from 9.45 A to 9.43 A by irradiating the tooth with a visible or near visible light beam, preferably having wavelengths in the range of between from about 400 nm to about 810 nm. Preferably at an energy density below about 65 J/cm$^2$, even more preferably below 30 J/cm$^2$, even more preferably, below about 12 J/cm$^2$. Preferably, the a axis is reduced at a temperature less than 250° C.

A further embodiment is a method of treating a tooth by changing the phosphate/calcium ratio in a portion of a tooth by more than 10% using electromagnetic radiation, preferably having a wavelength between about 400 nm to about 810 nm. Preferably, the electromagnetic radiation is of a wavelength which is substantially transmissible through water. Preferably, the calcium phosphate ratio is changed at a temperature less than about 250° C.

A further embodiment of the invention is a home treatment kit for the treatment of a tooth containing a fluoride mixture for application to the tooth, a light source which produces wavelengths in the range of between about 400 nm to about 750 nm adapted to illuminate the fluoride mixture, and at least one of a fluoride mouthwash, and a fluoride patch.

A further embodiment of the invention is a method of treating a tooth by irradiating the organic molecules within the tooth structure to reduce the solubility of the tooth to acid. Preferably, the method is applied to the tooth enamel, dentin, or cementum. Preferably, the treatment heats the tooth structure to a temperature less than about 250° C. Preferably, the method results in a permanent or semi-permanent change to the solubility of the tooth.

A further embodiment of the invention is a method of treating a tooth, by changing the structure and composition of a tooth to include $P_2O_7$ as measured by x-ray diffraction by irradiating said tooth with a visible or near visible light beam, preferably at a heat less than 250° C.

A further embodiment is a method of treating a tooth by changing the structure and composition of the tooth to decrease the amount of carbonate in said tooth by irradiating said tooth with a visible or near visible light beam. Preferably, the structure is changed at a heat less than 250° C.

DETAILED DESCRIPTION OF THE PREFERRED EMBODIMENTS

The present invention describes a method which changes the solubility of a tooth without significant production of heat, in fact the present invention produces changes in the tooth at temperatures less than 250° C. The present invention also allows for a deeper treatment of the tooth, as well as the use of a lower concentration of fluoride, and has the potential to allow one to keep teeth completely free of caries for the lifetime of the patient. The method uses a visible light beam (or electromagnetic radiation) alone or in combination with a chemical agent to prevent dental caries. Surprisingly, while the action of a visible light beam and the action of fluoride both act separately to increase resistance of the tooth to decay, the action of the two together is not additive, but synergistic.

While not limiting the scope of the invention to any particular theory or mechanism of action, the following theoretical considerations may explain the synergistic combination which is observed in the practice of this invention. Many of the theories and information about fluoride may be additionally found in Higuchi, et al. U.S. Pat. No. 4,877,401, herein incorporated by reference.

The application of the visible light beam of the correct wavelength, (i.e. an argon laser beam) at low powers to the tooth acts on the "thermal sites" at a much reduced temperature (usually around 100° C.) and produces considerably less heat then $CO_2$ or comparable lasers. The visible light beam reduces the carbonated phase of the hydroxyapatite, making the tooth more resistant to attack. The removal or vaporization of carbonate lowers the solubility and changes the water content of the hydroxyapatite. It also changes the phase of the hydroxyapatite and makes it more pure. There is a reduction in the size of the hydroxyapatite crystal as well as an increased hardness in the tooth structure. The treatment may heat local sites in proximity to the surface, which have a high concentration of organic material and/or water. Finally the ratio of phosphate to calcium changes. All of these changes result in the increased capability of the tooth to resist demineralization, a precursor to tooth decay.

Fluoridation, or other chemical agents act on the "chemical sites" by binding to hydroxide radicals and sterically or chemically preventing the action of acid on those sites. However, fluoride can accumulate in the body and too much fluoride can result in fluorosis, a syndrome whereby teeth are discolored, resulting in white splotchy areas on the enamel during development. Children are particularly susceptible to fluorosis and can obtain the necessary concentration of fluoride simply from tap water and toothpaste which is accidentally swallowed during brushing. In addition, more serious diseases have been linked to too much fluoride including iodine deficiency disorders, confusion, drowsiness, and listlessness. Advantageously, in the present invention it was found that the laser treatment results in a situation in which less fluoride is necessary to provide the same result. Without being limited to a particular theory, it is thought that because of a shrinkage of the hydroxyapatite crystal, there are fewer "chemical" sites exposed and thus, less fluoride is necessary to provide the same protection.

The visible and near visible light beams can be coherent or noncoherent light sources. Lasers, coherent sources of light beams, useful in the present invention are those which generate sufficient power to increase the acid resistivity of tooth enamel at low power (producing less heat) which preferably fall within the visible part of the infrared. More preferably, the lasers possess one or more wavelengths which are not absorbed by water, but are absorbed by organic compounds. Preferably, the wavelengths are between about 400 and 810 mn, more preferably between about 457 and 514 nm. Preferably, the wavelengths correspond visibly to blue, green, yellow or red light. Examples of such lasers include argon lasers and diode lasers.

Alternatively, the visible light beams can be noncoherent sources which generate sufficient power to increase the acid resistivity of tooth enamel at low power (producing less heat), such as a light emitting diodes (LEDs). Preferably, the wavelengths are between about 400 and 810 nm, more preferably between about 457 and 514 nm. Preferably, the wavelengths correspond visibly to blue, green, yellow or red.

The lasers need only be used at low power to produce the desired effect. For argon lasers the light beam has an energy density below about 65 J/cm$^2$, preferably about 30 J/cm$^2$, preferably an energy density below about 12 J/cm$^2$.

The chemical agents may have very different mechanisms of action, but include: ethane-1-hydroxy-1,1-di-phosphonic acid, fluoride, dodecylamine HCl, and most preferably fluoride.

A variety of fluoride treatments can be used alone or in combination. For example, the fluoride can be applied as a paste before treatment with the laser or after treatment with the laser. The fluoride can be applied as a mouthwash or as part of a toothpaste. The fluoride may also be applied as a patch, providing a low concentration of fluoride in a timed-release manner. For example, mucoadhesive fluoride tablets consisting of a bioerodible matrix which dissolves completely after depletion can be used such as those described in Bottenberg et al. J Dent. Res. 77(1): 68–72.

Fluoride (Fl-) interacts at several stages of the caries process to inhibit progression or enhance reversal. The following three mechanisms of action are now considered to be the most important way in which fluoride works. First, fluoride has antibacterial properties at lower pH in the plaque when it enters the bacterial cell as HFl. When fluoride enters the bacteria it interferes with the enzymes inside the bacteria, slowing down or inhibiting acid production. Second, when fluoride is present in the aqueous phase on and within the tooth at the same time as an acid challenge, it dramatically inhibits dissolution of calcium and phosphate at the crystal surfaces in the subsurface regions of enamel. If fluoride is present in the tooth crystals where it is incorporated systematically during tooth development, it will dissolve out during the demineralization process and help to inhibit subsequent demineralization. Lastly, fluoride present in the aqueous phase at the crystal surfaces within the tooth speeds up the recrystallization by helping to bring calcium and phosphate ions together. This provides a much more acid-resistant "new" crystal surface. During subsequent acid challenges following ingestion of fermentable carbohydrates the acid bypasses this resistant mineral, and is forced to go deeper into the tooth before mineral can be dissolved making decay less and less likely to progress. Remineralization following demineralization in this way makes the tooth more and more resistant as time progresses with these natural pH-cycles.

In the prior art most of the changes to the tooth which are caused by heat occur at 1200° C., some changes occur between 500° C. and 1000° C. and a few are cited at temperatures as low as 250° C. to 400° C. In the proposed invention the changes occur as low as 100° C., because the organic material vaporizes at about 100° C. However, the changes may occur as low as 50° C., including 60° C., 70° C., 80° C., 90° C., and the method may work at lower temperatures, including 40° C.

Below are examples of specific embodiments for carrying out the present invention. The examples are offered for illustrative purposes only, and are not intended to limit the scope of the present invention in any way.

Previous results from the present inventors showed that laser treatment with an argon laser results in a decrease in demineralization of the tooth. This is important because demineralization is the precursor to decay. Therefore, it was of particular interest to determine what type of changes occur and what temperatures and energy densities are required to produce this effect. Example 1 shows for the first time in the literature that the a axis of hydroxyapatite can be changed by treatment with a laser at low heat.

EXAMPLE 1

Laser Treatment Results in a Reduction of 0.02 A in the "a" Axis of a Hydroxyapatite Crystal Enamel from 47 human teeth were subjected to treatment with an argon laser at various energy densities ranging from 65 to 283 J/cm$^2$ for 0.2 sec at 1 Hz. The enamel was then subjected to x-ray diffraction. Results from this treatment showed that there was a mechanical change in the a axis of the human enamel (HE) from 9.45 A to 9.43 A (see Table 1). Such a reduction was statistically significant. It is known in the literature that the hydroxyapatite of human enamel is more soluble than stoichiometric hydroxyapatite, which has an a axis of 9.418 A approaching that of lased enamel. This axis reduction is caused by a loss of structural water and a corresponding increase in structural hydroxide groups (OH—) along the a axis. Another causative factor is the vaporization of organic compounds such as carbonate which results in a prism structure with reduced voids where acids would preferentially attack when the tooth is exposed to acids in the saliva.

TABLE 1

| X-ray diffraction of teeth treated at 283 J/cm$^2$ | |
| --- | --- |
| a Axis/Lased | a Axis/Unlased |
| 9,425 | 9,444 |
| 9.43 | 9,446 |
| 9,438 | 9,442 |
| 9,443 | 9,448 |
|  | 9,459 |
| 9,434 | 9,447 |
| M: 9.434 | M: 9.448 |
| SD: 0.0073 | SD: 0.0060 |

Further changes to the crystal structure included a slight shift in the orientation of the c axis to the surface of the tooth and the appearance of a new $P_2O_7$ peak on x-ray diffraction of lased enamel as compared to unlased enamel. The appearance of the $P_2O_7$ peak was due to $HPO_4$ which was hydrolyzed due to the heat created by the vaporization of organic compounds releasing water resulting in an increase in the amount of $P_2O_7$ ($2HPO_4 \rightarrow P_2O_7 + H_2O$). Christofferson and Christofferson (1981) have shown that the appearance of this phase increases cavity resistance. The reduction of carbonate also decreases the enamel solubility and acid resistance. For example, adult teeth are more resistant to decay, because they contain less carbonate than primary teeth.

EXAMPLE 2

Laser Treatment Results in the Removal of Organic Compounds, Hardening the Hydroxyapatite Crystal The removal of organic compounds purified the hydroxyapatite crystal and increased the bond strength as shown in Example 1, therefore, the calcium phosphate ratio and hardness of the tooth were tested to determine the effect of the laser on the tooth.

For the ESCA analysis, enamel from 7 human teeth was subjected to treatment with an argon laser at various energy densities ranging from 65 to 283 J/cm$^2$ for 0.2 sec at 1 Hz. The calcium phosphate ratio (atomic ratio) as shown by electron spectroscopy chemical analysis (ESCA) changed from 1.3 for unlased enamel to 1.14 for lased enamel, a decrease of 12% (see Table 2). This confirmed the removal of organic compounds by the laser treatment.

TABLE 2

ESCA data

| Ca/P; Lased | Ca/P; Unlased |
|---|---|
| 1.01 | 1.14 |
| 1.23 | 1.47 |
| 1.21 | 1.39 |
| 0.97 | 1.32 |
| 1.28 | 1.38 |
| 1.11 | 1.34 |
| 1.19 | 1.11 |
| Mean = 1.14 | Mean = 1.30 |
| SD = 0.1167 | SD = 0.1333 |

Result: Significant at 95%; T-2.45 with 12 degrees of freedom

For the Vickers Hardness test, enamel from 4 human teeth was subjected to treatment with an argon laser at various densities including 425 J/cm$^2$ for 0.2 sec at 1 Hz. Three measurements were taken per tooth. The Vickers hardness test demonstrated that hardness was correspondingly increased, showing that removal of the organic compounds also increased the hardness of the tooth (see Table 3). Unlased enamel had a mean Vickers hardness of 299 Kg/mm$^2$, while lased enamel resulted in a mean hardness of 578 Kg/mm$^2$.

TABLE 3

Vickers Hardness (kg/mm$^2$) of human enamel

| Lased | Unlased |
|---|---|
| 525 | 246 |
| 520 | 310 |
| 510 | 240 |
| 565 | 360 |
| 580 | 325 |
| 585 | 280 |
| 610 | 335 |
| 615 | 265 |
| 610 | 255 |
| 605 | 245 |
| 610 | 360 |
| 595 | 370 |
| M: 577.5 | M: 299.25 |
| SD: 38.700 | SD: 49.757 |

T student test: Unpaired and two-tailed test extremely significant at 95%; T = 15.29 with 22 degrees of freedom.

EXAMPLE 3

Laser Treatment in Combination with Fluoride Treatment Results in the Removal of Organic Compounds and a Hardening of the Hydroxyapatite Crystal at a Deeper Level Enamel from human teeth is treated with a fluoride paste at a concentration of 200 ppm (0.08%) Fl of stannous fluoride. The treated enamel is then subjected to treatment with an argon laser at 12–30 J/cm$^2$ for 10 seconds for each treated surface. Treatment efficacy is compared to enamel treated with fluoride alone or argon laser alone.

It was previously shown that treating the tooth with very high heat (250° C. to more than 1000° C.) resulted in less structural water and carbonate reduction only at the surface of the enamel thus changing the a axis of the crystal structure. Several researchers have tried to reproduce these results using lasers that were highly absorbed at the surface of the enamel (CO$_2$ and Er:YAG) or lasers with a dye initiator to create surface heat (argon and Nd:YAG). However, the problem of safety and the ability to treat the tooth at a more than surface-level remain. The use herein of an argon laser, however, provides for a much safer and surprisingly a deeper treatment of the tooth at lower temperatures, typically around 100° C. At these low dosimetries (and heats), the argon laser is safer and still penetrates more deeply due to its lower absorption, vaporization of the organic molecules including carbonate and hydrolyzation of the HPO$_4$ molecule. The removal of H+ at the surface as well as below the surface and the removal of water within the tooth structure allows for the bonding of fluoride at deeper levels of the hydroxyapatite. Unlike the literature, which hypothesizes only a surface effect of fluoride to further increase the resistance to demineralization (from 10 to 20 $\mu$), the present method provides for the bonding of fluoride to the hydroxide molecule in decreasing concentrations as one descends from the surface of the enamel towards the pulp, providing a much deeper effect on the tooth (to at least 1 mm).

EXAMPLE 4

A Lower Concentration of Fluoride (Fl) is Needed to be Effective

Enamel from a Human Tooth is Treated with a Fluoride Paste at a Concentration of 200 ppm (0.08%) Fl of stannous fluoride or 1000 ppm (0.22%) Fl of sodium fluoride. The treated enamel is then subjected to treatment with an argon laser at 12–65 J/cm$^2$ for 0.2 to 10 seconds for each treated surface. The treatment effectiveness is compared to a comparable treatment using much higher (5-fold) concentrations of fluoride.

Previous results using a CO$_2$ laser have shown that the amount of fluoride applied to the tooth after laser treatment can be reduced by about five-fold for an effective treatment. Therefore, the effective concentration of fluoride applied before or after laser treatment is reduced approximately five fold in the present method. Typically, this results in a reduction of the concentrations needed from normal concentrations of 1000 ppm Fl of stannous fluoride (0.4%) or 5000 ppm Fl of sodium fluoride (1.1%) to 200 ppm (0.08%) or 1000 ppm (0.22%) or less. The same applies to mouthwash and patches containing fluoride which typically require 225 ppm Fl (0.05%) to 0.01 ppm Fl, and are used following the laser procedure to maintain the resistance of the tooth to acids.

Even with the lower concentration of fluoride the bonding of fluoride to the hydroxide molecules occurs to a much deeper level of the tooth then previous methods. Without being restricted to a specific theory, the vaporization of the water may leave an ion imbalance which creates a structure with an affinity for fluoride. Thus, less fluoride is required to get a prophylactic effect.

EXAMPLE 5

The Fluoride Treatment in Combination with the Laser Treatment Produces a Synergistic Effect When the laser treatment as presented in Example 1 is used in combination with the fluoride treatment a synergistic effect occurred and this was partly responsible for the need for less fluoride. This is shown by the fact that the results in Examples 3 and 4 with both fluoride and argon laser treatment are more then additive when compared to those with fluoride alone or laser treatment alone.

Previous results using a CO$_2$ laser have shown that in addition to a reduced amount of fluoride for an effective treatment, the laser treatment plus the low concentration fluoride treatment results in a synergistic effect. Results presented in Examples 1–3 show that the low energy argon laser provides the same effect in a safer manner as that of the $CO_2$ laser. Therefore, treatment of the tooth with an argon laser in combination with fluoride treatment provides a similar synergistic effect to that of $CO_2$ treatment with fluoride treatment.

EXAMPLE 6

Vickers Hardness Test of Laser Treated Teeth with and without Fluoride Treatment Enamel from 4 human teeth is treated with a fluoride paste at a concentration of 200 ppm (0.08%) Fl of Stannous Fluoride or 1000 ppm (0.22%) Fl of sodium fluoride. The treated enamel is then subjected to treatment with an argon laser at 250 MW, 10 Hz for 0.2 to 10 seconds for each treated surface. Three measurements were per tooth and the mean value is shown below.

The results were as follows, given as the mean of Vickers hardness values:

Enamel 306

Enamel+Laser 577

Enamel+Fluoride 289

Enamel+Fluoride+laser 297

The results suggest that the fluoride initally softens the tooth perhaps due to its acidity. When the laser is applied after the fluoride is added, it returns the tooth back to its initial hardness.

The results are shown in Tables 4, 5, and 6.

TABLE 4

Vickers Hardness with and without fluoride

| ENAMEL (A) | E + F (B) | L + F (C) |
|---|---|---|
| 302 | 227 | 255 |
| 335 | 329 | 297 |
| 319 | 300 | 305 |
| 311 | 298 | 257 |
| 313 | 349 | 287 |
| 307 | 283 | 269 |
| 307 | 280 | 293 |
| 326 | 313 | 286 |
| 312 | 312 | 269 |
| 284 | 339 | 310 |
| 281 | 340 | 336 |
| 297 | 282 | 294 |
| 276 | 280 | 280 |
| 298 | 279 | 295 |
| 246 | 279 | 300 |
| 269 | 228 | 241 |
| 282 | 313 | 317 |
| 287 | 245 | 276 |
| 283 | 246 | 243 |
| 277 | 282 | 260 |
| 268 | 238 | 314 |
| 308 | 323 | 313 |
| 260 | 287 | 316 |
| 354 | | 344 |
| 291 | | 319 |
| 274 | | 326 |
| 271 | | 305 |
| 322 | | 315 |
| 296 | | 302 |
| 310 | | 317 |
| 307 | | 300 |
| 327 | | 272 |
| 392 | | 309 |
| 337 | | 301 |
| 286 | | 304 |
| 362 | | 324 |
| 345 | | 326 |
| 313 | | 320 |
| 324 | | 279 |

TABLE 4-continued

Vickers Hardness with and without fluoride

| ENAMEL (A) | E + F (B) | L + F (C) |
|---|---|---|
| 307 | | 285 |
| 323 | | 304 |
| 291 | | 310 |
| 308 | | 294 |
| 282 | | 298 |
| 340 | | 259 |
| 367 | | 315 |
| 307 | | 329 |
| 242 | | 323 |
| 269 | | 257 |
| 293 | | 316 |
| 276 | | 300 |
| 278 | | 282 |
| 319 | | 302 |
| 299 | | 300 |
| 316 | | 298 |
| 299 | | 288 |
| 309 | | 308 |
| 293 | | 298 |
| 335 | | 311 |
| 315 | | 286 |
| 305 | | 323 |
| 317 | | 304 |
| 270 | | 248 |
| 319 | | 298 |
| 342 | | 284 |
| | | 332 |
| | | 300 |
| | | 275 |

A + B = Significant
A + C = Significant
B + C = Not Significant (T = 1.22 with 89 degrees of freedom) the two tailed p value is 0.2264; 95% Confidence interval of the difference. Total 159 tests
(E & EF)

TABLE 5

A & B = Mean

| Mean A | Mean B |
|---|---|
| 306 | 289.2609 |
| NB = 65 | NB = 26 |
| Std Dev = 29.77795 | 35.53264 |
| Min = 242 | 227 |
| Max = 392 | 349 |

T = 2.18 with 86 degrees of freedom
The two-tailed p value is 0.0320; Significant
95% Confidence interval of the difference
(EF & LF)

TABLE 6

A & C

| Mean A | Mean C |
|---|---|
| 306 | 297.1324 |
| NB = 65 | NB = 68 |
| Std Dev = 29.77795 | 23.04506 |
| Min = 242 | 241 |
| Max = 392 | 344 |

T = 2.09 with 64 degrees of freedom
The two tailed p value is 0.0408; Significant
95% Confidence interval of the difference

EXAMPLE 7

Method of Treating a Tooth Using an Argon Laser

The Argon laser is applied to the tooth at 250 mW (or 12 to 65 J/cm$^2$) for 0.2 to 10 sec at a 5 mm diameter spot size on the tooth surfaces. Prior to lasing, the teeth were prophied (cleaned) and a low concentration of fluoride gel was applied. Alternatively, the fluoride gel may be applied after laser treatment. Maintenance treatment includes using a fluoride mouthwash containing low concentrations of fluoride once a day, and fluoride patches containing low concentrations of fluoride applied weekly. The teeth are laser treated every 2 to 5 years.

EXAMPLE 8

Method of Treating a Tooth Using a Visible LED

The tooth is treated as in Example 6, however an LED is used in place of the argon laser. The LED is used at a wavelength from the IR spectra of green, blue, yellow, or red.

EXAMPLE 9

Method of Treating a Tooth Using an Argon Laser in Combination with Fluoride The tooth is treated with fluoride at a concentration of about 200 ppm (0.08%) Fl of stannous fluoride or 1000 ppm (0.22%) Fl of sodium fluoride. The Argon laser is applied to the tooth at 250 to 300 mW for 10 sec (or longer) at an 8 mm diameter spot size on each of the surfaces. Prior to lasing, the teeth were prophied (cleaned) and a low concentration of fluoride gel was applied. Maintenance treatment includes using a fluoride mouthwash containing low concentrations of fluoride once a day, and fluoride patches containing low concentrations of fluoride applied weekly. The teeth are laser treated every 2 to 5 years.

EXAMPLE 10

Kit for At-Home Use

The kit includes a hand-held light source, LED with a shield which protects the patient from laser reflections which may damage their eyes, while still allowing viewing of the process, a fluoride treatment for application to the tooth before laser treatment, a mouthwash with a low fluoride concentration, and patches with a low fluoride concentration for follow-up use. The patient applies the fluoride, treats the tooth with the laser, uses the mouthwash daily, and attaches the patch once a week or once a month. This allows the patient to keep the teeth caries-free as long as treatment is continued. However, treatment may still be effective without the addition of the mouthwash or the patch.

EXAMPLE 11

Kit for Professional Use

The kit includes a fluoride treatment containing a low concentration of fluoride, a means for applying the fluoride to the tooth, sample mouthwash and sample patches for the patient to take home. Various types of light sources can be used by the professional.

What is claimed is:

1. A home treatment system for the treatment of a tooth comprising:

a fluoride mixture for application to the tooth, a light source which produces wavelengths in the range of between about 400 nm to about 750 nm, wherein said light source is able to bind the fluoride mixture to at least a portion of the tooth;

wherein said light source has an energy density which does not cause substantial structural damage to the tooth; and wherein said fluoride mixture comprises fluoride at a concentration in the range of about 0.002 ppm fluoride to about 45 ppm fluoride.

2. A home treatment system for the treatment of a tooth comprising:

a fluoride mixture for application to the tooth, a light source which produces wavelengths in the range of between about 400 nm to about 750 nm, wherein said light source is able to bind the fluoride mixture to at least a portion of the tooth;

wherein said light source has an energy density which does not cause substantial structural damage to the tooth; and wherein said fluoride mixture comprises fluoride at a concentration of about 0.01%.

3. The system of claim 2, wherein said fluoride mixture is a gel or a paste.

4. The system of claim 1, further comprising a fluoride maintenance source, wherein said fluoride maintenance source is selected from the group consisting of one or more of the following: a fluoride mouthwash, a fluoride patch, and a fluoride toothpaste.

5. The system of claim 1, wherein said light source is able to bind the fluoride mixture to at least a portion of the tooth by illuminating the fluoride mixture while said fluoride mixture is positioned on the tooth.

6. The system of claim 1, wherein said light source is able to bind the fluoride mixture by chemically modifying the tooth to facilitate binding of said fluoride mixture.

7. The system of claim 6, wherein said chemical modification occurs prior to application of the fluoride mixture to the tooth.

8. The system of claim 1, wherein said light source is able to facilitate subsurface penetration of fluoride.

9. The system of claim 1, wherein said light source is able to heat the tooth to a temperature of less than about 250° C.

10. The system of claim 1, wherein said light source is able to provide an energy density of less than about 65 J/cm$^2$.

11. The system of claim 1, wherein said light source is able to provide an energy density of less than about 30 J/cm$^2$.

12. The system of claim 1, wherein said light source is able to provide an energy density of less than about 12 J/cm$^2$.

13. The system of claim 1, wherein said light source is a coherent light source.

14. The system of claim 13, wherein said coherent light source is a laser.

15. The system of Claim 14, wherein said laser is an argon laser.

16. The system of claim 14, wherein said laser comprises a diode laser.

17. The system of claim 16, wherein the wavelength of said diode laser is selected from the group consisting of one or more of the following: red, green, blue, and yellow.

18. The system of claim 1, wherein said light source is a noncoherent light source.

19. The system of Claim 18, wherein said noncoherent light source is an LED.

20. The system of Claim 18, wherein said noncoherent light source has a wavelength selected from the group consisting of one or more of the following: green, blue, yellow, and red.

21. A home treatment system for the treatment of a tooth comprising:

a fluoride mixture for application to the tooth, wherein the fluoride mixture is a gel or a paste;

a light source which produces wavelengths in the range of between about 400 nm to about 750 nm, wherein said light source is able to bind the fluoride mixture to at least a portion of the tooth;

wherein said light source has an energy density which does not cause substantial structural damage to the tooth; and wherein said fluoride mixture comprises fluoride at a concentration in the range of about 0.002 ppm fluoride to about 45 ppm fluoride.

* * * * *